United States Patent [19]
Elkhoury

[11] Patent Number: 5,834,480
[45] Date of Patent: Nov. 10, 1998

[54] TOPICAL APPLICATION OF OPIOIDS FOR TREATMENT OF ACNE AND SEBACEOUS GLAND DISORDERS

[76] Inventor: George F. Elkhoury, 1561 Ramillo Beach Ave., Long Beach, Calif. 90815

[21] Appl. No.: 874,254

[22] Filed: Jun. 13, 1997

[51] Int. Cl.⁶ .................................................. A61K 31/44
[52] U.S. Cl. .......................... 514/289; 514/859; 514/864; 514/887
[58] Field of Search ............................................. 514/289

[56] References Cited

U.S. PATENT DOCUMENTS

| | | | |
|---|---|---|---|
| 4,416,886 | 11/1983 | Bernstein | 424/260 |
| 5,589,480 | 12/1996 | Elkhoury et al. | 514/282 |

FOREIGN PATENT DOCUMENTS 2287404  9/1995  United Kingdom .

OTHER PUBLICATIONS

Bergfeld, W.F. "The evaluation and management of acne: Economic Considerations," J. Am.Acad. Dermatol., vol. 32, pp. S52–S56.
Berson, D.S. and Shalita, A.R. "The treatment of acne: The role of combination therapies," J. Am. Acad. Dermatol., vol. 32, pp. S31–S41.
Dickenson, "Neurophysiology of Opioid Poorly Responsive Pain," Cancer Surveys, vol. 21: Palliative Medicine: Problem Areas in Pain and Symptom Management.
Kaminer, M.S. and Gilchrist, B.A., "The many faces of acne," J. Am.Acad. Dermatol, vol. 32, pp. S6–S14, May.
Kinnman, et al., "Peripherally Administered Morphine Attenuates Capsaicin–Induced Mechanical Hypersensitivity in Humans," Anesth Analg, pp. 595–599.
Koo, J., "The psychosocial impact of acne: Patients' perceptions," J. AM. Acad. Dermatol., vol. 32, pp. S31–S41, May.
Giardina et al., "Central and Peripheral Analgesic Agents: Chemical Strategies for Limiting Brain Penetration in Kappa–Opioid Agonists Belonging to Different Chemical Classes," Il Farmaco, pp. 405–418.
Herz, "Role of Immune Processes in Peripheral Opioid Analgesia," in The Brain Immune Axis and Substance Abuse, Plenum Press, New York, pp. 193–199.
Makman, "Morphine Receptors in Immunocytes and Neurons," Advances in Neuroimmunology, vol. 4, pp. 69–82.
Mather,"Opioids: A Pharmacologist's Delight!" Australasian Society of Clinical Experimental Pharmacologists and Toxicologists Symposium, 1994, Clinical and Experimental Pharmacology and Physiology, pp. 833–836.
Needham,"Painless Lumbar Surgery:Morphine Nerve Paste," Connecticut Medicine,vol. 60, No. 3, pp. 141–143.
Nguyen, Q.H. et al., "Management of Acne Vulgaris," American Family Physician, vol. 50, No. 1, pp. 89–96.
Peyman et al., "Effects of morphine on corneal sensitivity and epithelial wound healing: implications for topical ophthalmic analgesia," British Journal of Opthamology, pp. 138–141, Feb.
Sharp et al.,eds., The Brain Immune Axis and Substance Abuse, Chap. 27, Plenum Press, New York.
Siddall and Cousins, "Pain Mechanisms and Management : an Update," Clinical Experimental Pharmacology and Physiology, pp. 679–688.
Solomon, B.A., and Shalita, A.R., "Effects of Detergents on Acne," Clinics in Dermatology, vol. 14, pp. 96–98.
Stein et al., "Antiociceptive effects of mu–and kappa–agonists in inflammation are enhanced by a peripheral opioid receptor–specific mechanism of action," Eur.J. Pharmacol., pp. 255–264.
Stein et al., "No Tolerance to Peripheral Morphine Analgesia in Presence of Opioid Expression in Inflamed Synovia," J. Clin. Invest., vol. 98, No. 3, pp. 793–799, Aug.
Stein et al., "Opioids as novel intra–articular agents in arthritis," Progess in Pain Research and Management, Fields,H.L. and Liebeskind, J.C., eds., IASP Press, Seattle, pp. 289–296.
Stein et al., "Peripheral effect of fentanyl upon nociception in inflamed tissue of the rat," Neurosci. Lett., pp. 225–228.
Sykes, N.L. Jr. and Webster, G.F., "Acne: A Review of Optimum Treatment," Drugs, vol. 48, No. 1, pp.59–70, 1994.
Traynor, "Opioid Receptors and Their Subtypes: Focus on Peripheral Isolated Tissue Perparations," Neurochem, Int, vol. 24., No. 5, pp. 427–432.
"Acne in Teens: Ways to Control It" a handout adapted from brochure in AAFP Patient Education Brochure Series, Health Notes from Your Family Doctor, Jul.
Chemical Abstracts vol. 124: 3777g MacLean (U.K.application2,287,404; 1995), 1996.

*Primary Examiner*—Leonard Schenkman
*Attorney, Agent, or Firm*—Greenblum & Bernstein, P.L.C.

[57] ABSTRACT

Treatment of acne through topical administration is an aspect of the present invention. Specifically, opioids may be applied in any therapeutically acceptable carrier including gels, creams, lotions, and sprays. Therapeutic effects observed with the present invention include decrease in redness, swelling, and inflammation. Treatment of other inflammatory conditions is also disclosed. Treatment of suitable conditions in accordance with the present invention results in significant improvements in healing of those conditions.

26 Claims, No Drawings

TOPICAL APPLICATION OF OPIOIDS FOR TREATMENT OF ACNE AND SEBACEOUS GLAND DISORDERS

BACKGROUND OF THE INVENTION

1. Field of the Invention

The present invention is directed to the treatment of acne and other inflammatory conditions. More specifically, in some embodiments this invention relates to methods for treating acne which methods comprise the topical application of opioids. Treatment in accordance with the present invention results in improved healing in the treated area.

2. Background of the Invention and Related Information

Acne is one example of inflammatory conditions which may be treated in accordance with the present invention.

Acne is a multifactorial disease affecting the sebaceous follicle and characterized by papules, pustules, and scars. Acne affects nearly 90% of 16-year old boys and girls but is clearly no longer a problem confined to teenagers. Recently for this condition, referral for specialists' opinions have significantly increased among people over the age of 20. It has been realized that simple attention to hygiene is no longer sufficient, and antiseptic washes so popular some years ago are now perceived as ineffective by many sufferers and most clinicians.

During puberty, elevated androgen levels stimulate the sebaceous glands to enlarge and produce increased amounts of sebum in the sebaceous follicle. Subsequent abnormal keratinization with hyperkeratosis of the follicular epithelium leads to obstruction of the duct by horny plaque. The blocked duct becomes clogged with a dense material composed of sebum and keratinous debris forming a microcomedo, a precursor of the acne lesion. Further distention leads to open and closed comedones that are noninflammatory lesions. The excess sebum in the microcomedo also provides an anaerobic growth medium for *Propionibacterium acnes*. Lipase from the bacteria hydrolyzes sebum triglycerides into free fatty acids that are both comedogenic and proinflammatory. *Propionibacterium acnes* also secretes chemotactic factors that attract neutrophils. Lysosomal enzyme released from the neutrophils rupture the follicle wall releasing proinflammatory mediators including keratin and lipids into the surrounding derrius. Inflammatory papules appear as a result. Further inflammation with macrophages and foreign body reactions lead to cysts and nodules. The key features of the pathogenesis of acne can be characterized as 1) increased sebum production, 2) follicular corynekeratinization, 3) bacterial proliferation, and 4) inflammation.

Effective management of acne can be accomplished by addressing the four key features of the pathogenesis. Topical therapy is usually the first choice for patients with mild-to-moderate inflammatory acne. The use of topical therapy minimizes potential side effects associated with the use of systemic agents. Topical therapies include benzoyl peroxide, which is the most commonly used non-prescription acne medication. It is an important antibacterial oxidizing agent that can decrease the number of *Propionibacterium acnes* and frequently the amount of free fatty acids. Benzoyl peroxide is the first line monotherapy for mild acne and it is available in over-the-counter preparations. Benzoyl peroxide is applied once or twice daily and patients often experience mild redness and scaling of the skin during the first week of usage.

Tretinoin is the most effective topical comedolytic agent, decreasing the cohesiveness of follicular epithelial cells, and thereby inhibiting the formation of microcomedones and increasing cell turnover resulting in expulsion of existing comedones. This agent also decreases the thickness of the stratum corneum and potentiates the penetration of topical antibiotic agents. Tretinoin therapy comprises once daily application. Mild redness and peeling are a part of the therapeutic effect of the medication but can result in reduced patient compliance. Patients should be made aware that improvement may take as long as 6 to 12 weeks, and that flare-ups of acne can occur during the first few weeks of therapy. In addition, it is extremely important that patients avoid excessive exposure to the sun during treatment.

Mild inflammatory acne lesions can also be treated with topical antibiotics including erythromycin ointment, clindamycin solution, and meclocylcine cream. The primary action of the antibiotics is to reduce the opoulation of *Propionibacterium acnes* in the sebaceous follicle and thereby suppress the free fatty acid production. The effectiveness of topical antibiotics in the treatment of acne is limited by their low lipid solubility and subsequent difficulty in penetrating sebum-filled follicles. Topical antibiotics are applied twice daily.

Patients with moderate to severe inflammatory acne often require oral antibiotics in addition to topical therapy. The most commonly prescribed agents include tetracycline, erythromycin, minocycline, and doxycycline. Treatment is usually maintained for several months. Side effects include the overgrowth of nonsusceptible organisms, including Candida, which can produce vaginal and oral yeast infections.

Patients with severe inflammatory acne unresponsive to other therapy may require treatment with oral isotretinoin. Isotretinoin is a compound related to vitamin A, and is the only agent that decreases sebum production and reverses the abnormal epithelial formation process. This agent can also decrease the pupulation of *Propionibacternum acnes* in the sebaceous follicle. Duration of therapy is usually 20 weeks, and the satisfactory response rate is quite high. Treatment is often accompanied by many side effects, however, including dry skin, pruritus, epistaxis, and photosensitivity, as well as hypertriglyceridemia, abnormal liver function tests, electrolyte imbalances, and elevated platelet counts. Most serious though, is the teratogeric effect of isotretinoin. Use of isotretinoin during pregnancy is absolutely contraindicated. So serious is the potential for death or teratogenic effects to a fetus, isotretinoin is practically contraindicated in women of child-bearing age. Use of isotretinoin must be accompanied by a guarantee by the patient that conception will be avoided at any and all costs.

Because acne is a multifactorial disease which is manifest to varying degrees, it is important for the physician to assess the patient to attempt to find therapies which will be helpful to the patient without causing major side effects. All of the current conventional treatments are associated with some degree of adverse side effects that limit their usefulness. Consequently, there is a need for a drug that eliminates acne without side effects.

In the past, administration of opioids has been directed at targeting opioid receptors in the central nervous system (CNS). In addition to their presence in the CNS, opioid receptors have been found on sensory nerves in inflamed subcutaneous tissue. This finding was reported in Stein et al., "Peripheral effect of fentanyl upon nociception in inflamed tissue of the rat," *Neurosci. Lett.* 84:225–228 (1988), and in Stein et al., "Antinociceptive effects of mu- and kappa-agonists in inflammation are enhanced by a peripheral opioid receptor-specific mechanism of action," *Eur. J. Pharmacol.* 155:255–264 (1988). Small doses of opioids, when applied locally or topically in inflamed areas outside the central nervous system, can produce local analgesic effects by interacting with the opioid receptors on peripheral sensory nerves and producing local analgesia. This finding was discussed in Stein et al., "Opioids as novel intra-articular agents in arthritis," In: *Progress in Pain Research and Management,* Fields, H. L., and Liebeskind, J. C., eds., 1:289–296, IASP Press, Seattle, (1994). A practical application of this phenomena is presented in U.S. Pat. No. 5,589,480, to Elkhoury et al., wherein the topical application of an opioid analgesic agent to alleviate pain is disclosed. Reference is also made to the present inventor's copending U.S. patent application Nos. 08/741,743, and 08/732,594, both of which are directed to the topical application of opioid analgesic agents. Still further reference is made to the present inventor's copending U.S. patent application No. 08/854,323, which is directed to the use of opioid analgesic agents in the treatment of pain. U.S. patent application Nos. 08/741,743, 08/732,594, and 08/854,323, are hereby incorporated by reference as though set forth in full herein.

Peripheral opioid effects are not initially apparent in normal tissue, but do become apparent within minutes to hours at the site of inflammation. It is believed that the reason for the pain relief is that opioids can gain easier access to neuronal opioid receptors during inflammation as a result of the disruption of the perineurium (which is normally an impermeable sheath encasing the peripheral nerve fiber). Further, the number of peripheral sensory nerve terminals is increased in inflamed tissue and a phenomenon known as sprouting occurs in which the number of fibers increases significantly within inflamed tissue. The sprouting results in a subsequent increase in the number of morphine receptors that are peripherally accessible to locally-applied opiods.

In addition to their presence in the peripheral nervous sytem, opioid receptors have been identified in the immune system as well. Specific opioid receptors, identified at $\mu_3$ receptors, have been identified on white blood cells, including macrophages and peripheral blood granulocytes, both of which are involved in the immune response in humans. In addition, it has been shown that some lymphocytes, as well as some monocytes and macrophages, produce endogenous opioid peptides. These findings have led some researchers to suggest a neural-immune link. However, the manner in which these two systems intersect is still quite unclear. A review of opioid receptors in immunocytes and neurons is presented in *Advances in Neuroimmunology* Vol. 4, pgs. 69–82 (1994), the entire content of which is hereby incorporated by reference as though set forth in full herein. The role of immune processes in peripheral opioid analgesia is presented in Chapter 27 of *The Brain Immune Axis and Substance Abuse* (Sharp, B. et al., eds.) )Plenum Press, New York, 1995), the entire content of which hereby incorporated by reference as though set forth in full herein.

As discussed above, the formation of acne is frequently associated with inflammation. During the inflammatory process, white blood cells are attracted to the area of the lesion, and play a crucial role in fighting the infection. Other local infections are characterized by similar inflammatory processes. In addition, burns also trigger the body's inflammatory response.

SUMMARY OF THE INVENTION

In accordance with the present invention, it has been surprisingly found that topical application of opioids results in a significant reduction in acne lesions. Doses of opioids used in accordance with the present invention are very small, such that they produce no significant systemic effect. Further, in accordance with the present invention, the opioids may be applied in carrier vehicles which do not further aggravate acne lesions.

The present invention is directed to effectively treating inflammation of the skin.

The present invention is directed to effectively treating topical bacterial infections and inflammation associated therewith.

The present invention is further directed to effectively treating acne through the topical application of opioids, without the side effects associated with prior acne treatments.

The present invention is further directed to effective relief of the symptoms of acne through the use of topical opioid administration, thereby effectively reducing the acne lesions.

The present invention is further directed to effectively treating burns of the skin.

The present invention is further directed to effectively treating irritation of the skin comprising inflammation which is the result of noxious stimuli.

The present invention is achieved by the provision of methods of treating acne in a patient in need of such treatment comprising the topical administration of a therapeutically-effective amount of a composition comprising an opioid. Preferably, the composition comprises a gel or cream, which is preferably administered by spreading the gel or cream onto the affected area. In other preferred embodiments, the composition comprises a liquid, which is preferably administered by spraying onto the affected area. In preferred embodiments, the opioid is administered in an amount analgesically equivalent to up to 5 mg of morphine per 6 in$^2$ of skin. More preferably, the opioid is administered in a amount analgesically equivalent to 2–3 mg of morphine per 6 in$^2$ of skin. The opioid perferably comprises morphine. In other preferred embodiments, the opioid comprises morphine sulfate. In still other preferred embodiments, the opioid comprises butorphanol. Preferably, a unit dose of the opioid is in the range of from about 1/1000 of an intramuscular dose of the opioid to about 1/5 of a intramuscular dose of opioid. More preferably, a unit dose of said opioid is in the range of from about 1/100 of an intramuscular dose of the opioid to about 1/10 of an intramuscular dose of the opioid. Even more preferably, a unit dose of said opioid is in the range of from about 1/25 of an intramuscular dose of the opioid to about 1/15 of an intramuscualr dose of the opioid. Most preferably, a unit dose of the opioid is about 1/20 of an intramuscular dose of the opioid. In preferred embodiments, the acne comprises inflammatory acne. In other preferred embodiments, the acne comprises non-inflammatory acne.

The present invention is further achieved by the provision of methods of treating local inflammation of the skin comprising a bacterial infection, the method comprising the administration of a therapeutically-effective amount of an opioid. Preferably, the local inflammation of the skin comprises a Staphylococcus infection.

The present invention is further achieved by the provision of a method of treating skin disorders involving the sebaceous glands and follicles in humans comprising applying a therapeutically-effective amount of an opioid.

The present invention is further achieved by the provision of a method of treating acne in a patient in need of such treatment comprising the topical administration of a therapeutically effective amount of a composition comprising an opioid, wherein said administration is achieved via a topical dressing.

The present invention is further achieved by the provision of a method of expediting the remission of herpetic lesions of the skin comprising topically administering a therapeutically effective amount of an opioid to an area of skin affected by said herpetic lesions.

The present invention is further achieved by the provision of a method of expediting the healing of burns of the skin comprising topically administering a therapeutically effective amount of an opioid to an area of skin affected by said burn.

The present invention is further achieved by the provision of a method of reducing scarring in burn tissue comprising topically administering a therapeutically effective amount of an opioid to an area of skin affected by said burn.

The present invention is further achieved by the provision of a method of treating inflammation of skin comprising topically administering a therapeutically effective amount of an opioid to an area of skin affected by said inflammation, wherein said inflammation is in response to noxious stimuli. Preferably, the noxious stimuli comprises contact with caustic or corrosive chemicals. In other preferred embodiments, the noxious stimuli comprises contact with a plant, which is preferably selected from the group consisting of poison ivy, poison oak, and poison sumac. In other preferred embodiments the noxious stimuli comprises contact with a plant which comprises nettles. In other preferred embodiments, the noxious stimuli comprises a bite of an insect, which is preferably selected from the group consisting of biting flies, biting ants, and mosquitos. In other preferred embodiments, the noxious stimuli comprises the sting of an insect, which is preferably selected from the group consisting of bees, wasps, hornets, and stinging ants.

The present invention is further achieved by the provision of a method of treating acne in a patient in need of such treatment comprising topically administering a therapeutically effective amount of a composition comprising an opioid antagonist. Preferably the opioid antagonist comprises naloxone. In other preferred embodiments, the opioid antagonist comprises naltrexone.

DETAILED DESCRIPTION OF PREFERRED EMBODIMENTS OF THE INVENTION

The present invention is based at least in part on the surprising discovery that the topical, non-systemic, and preferably, non-transdermal, application of opioids is effective in significantly reducing and, therefore, treating skin inflammation in patients in need of such treatment. The prototypical opioid is morphine, but other opioids include, but are not limited to, compounds based on or derived from morphine-like compounds and analogs, including, but not limited to compounds such as, cyclazocine, piperidine, piperazine, pyrrolidine, morphiceptin, meperidine, trifluadom, benzeneacetamine, diarylacetamide, benzomorphan, alkaloids, peptides, phanantrene, and pharmaceutically acceptable salts, prodrugs, and derivatives thereof. Examples of preferred compounds which are specifically contemplated as opioids suitable for use in accordance with the present invention include, but are not limited to morphine, heroin, hydromorphone, oxymorphone, levorphanol, codeine, hydrocodone, oxycodone, buprenorphine, butorphanol, methadone, meperidine, fentanyl, propoxyphene, pentazocine, and nalbuphine. Other preferably compounds specifically contemplated include opioid antagonists such as naloxone and naltrexone. Pharmaceutically acceptable salts of the foregoing compounds may also be employed. Suitable opioids, including the foregoing, are also described in Chapter 23 of *Goodman and Gilman's Pharmacological Basis of Therapeutics, Ninth Edition,* (McGraw-Hill 1995), (pp. 521–555) which is hereby incorporated by reference as though set forth in full herein. It is expected that as the field of research in the present area expands, new opioids will be discovered. It is expected that such opioids will be effectively used in accordance with the present invention.

The choice of topical excipient as a vehicle for the anti-acne agent, while routine, is a significant consideration in the present invention for reasons which follow. An important criterion for selecting a suitable topical excipient is that it should not enhance the delivery of the opioid to the systemic circulation, e.g., transdermal or transmucosal transmission. As used herein, the term non-transdermal carrying agent is defined as a vehicle into which the opioid is diluted, which vehicle will not significantly enhance the migration of the opioid through the skin. Thus, non-transdermal carrying agents do not enhance the systemic delivery of the opioid. An additional consideration is that the excipient preferably will not exacerbate the acne condition. Preferred non-transdermal carrying agents include, but are not limited to, K-Y Gel™ or K-Y Jelly™, Eucerine™, lanolin, Vaseline™, and Aquaphor™. All of these non-transdermal carrying agents are contrasted with transdermal carrying agents such as DMSO, which can significantly enhance penetration and/or migration of a drug through the skin and thus the systemic delivery of the drug. A thorough description of acceptable pharmaceutical carrying agents can be found in many pharmaceutical science textbooks, including, for example, *Remington's Pharmaceutical Sciences, Eighteenth Edition,* (Mack Publishing Company 1990), the entire contents of which are hereby incorporated by reference as though set forth herein.

Additionally, acne may be treated in accordance with the present invention by administering the opioid suspended in or admixed with a suitable non-transdermal carrying agent and sprayed (either with a manually-actuated pump or with the aid of a suitable pharmaceutically-acceptable propellant) onto the affected skin of the patient in need of treatment. Suitable formulations for topical application of drugs by spraying the formulation containing the drug onto the skin are well known to those of ordinary skill in the art and can be routinely selected.

The topical application of opioids in accordance with the present invention reduces acne lesions Therapeutic effects of the present invention include, but are not limited to, decrease in redness and swelling of the affected area, reduction in the number of lesions in the affected area, and a general decrease in local inflammation. A primary advantage of the present invention is the excellent improvement in the condition without the typical side effects of conventional therapies. The potential for the present invention is widespread and the topical application of opioids shows promise as an exciting new method of acne treatment which does not exhibit the side effects associated with the prior art treatments.

While not wishing to be bound by theory, it is believed that the present invention may involve the interaction between the applied opioids and opioids and opioid receptors on white blood cells. The present scientific literature does not explain the practical role of such opioid receptors on white blood cells. Their presence has been demonstrated in vitro (see *Advances in Neuroimmunology* Vol. 4, pgs.

69–82 (1994), cited above and incorporated by reference), but their practical function is still unknown. In fact, unlike opioid receptors in the nervous system, an endogenous ligand for opioid receptors on white blood cells has not yet been identified. Therefore, their function on white blood cells is believed to be quite different from their function in the nervous system. From the results presented herein, it appears that the opioid receptors on white blood cells may be involved in mediating an immune response. It is believed that, for these reasons, the present invention is not only useful in the treatment of acne, but is also useful in the treatment of local inflammation of the skin, such as Staphylococcus infections and other localized skin infections, as well as burns, insect bites and stings, and superficial wounds.

It has surprisingly been found that treatment of suitable conditions in accordance with the present invention results in improved healing of the condition. For example, when used in the treatment of acne, lesions which are treated disappear faster than when left untreated, the size of the lesions decreases more rapidly, and redness in the area is more rapidly diminished as well. Normally herpetic lesions can take as long as 20 days to disappear without treatment. Very few treatments known in the art can decrease the healing time of herpetic lesions (decrease the time to remission). When treated in accordance with the present invention, however, herpetic lesions dry up more rapidly, stop oozing and forming pus sooner, and generally disappear more rapidly than when left untreated. In accordance with the present invention, healing time of herpetic lesions can be reduced to as little as 7 days. Depending on the severity (degree), burns can take weeks to heal and can leave considerable scar tissue after healing. In accordance with the present invention, burns not only heal more rapidly, but scarring is significantly reduced. Treatment of burns in accordance with the present invention will result in decrease in redness and swelling of the burned area. Scarring is less apparent when burns are treated in accordance with the present invention. Superficial wounds treated in accordance with the present invention also show considerably reduction in healing time, as well as reduction in the scarring of the area.

These unexpected improvements in healing in accordance with the present invention appear to contradict what is known in the art. For example, Peyman et al. demonstrate that epithelial wound closure in the cornea is not significantly different when the wound is treated with saline, or if the wound is treated with morphine sulfate (Br. J. Ophthalmol. (1994) Vol. 78, pgs. 138–141).

The following definitions in this specification are intended to be interpreted in an illustrative, rather than limiting sense. Therefore, they are to be interpreted inclusively, and are not to be limited to the specific definition recited.

A. Definitions

Agonist: a compound that displays an affinity for a receptor, and which enhances or stimulates the functional properties of the receptor. Examples of opioid agonists include but are not limited to, morphine, meperidine, depomorphine, methadone, etorphine, levorphanol, fentanyl, and sufentanyl.

Analgesia: relief of pain.

Analgesic: a compound that relieves pain; an opioid analgesic is an opioid that relieves pain by action on opioid receptors.

Antagonist: a compound that does not enhance or stimulate the functional properties of a receptor, yet blocks those actions by an agonist. Examples of opioid antagonists include but are not limited to naloxone and naltrexone.

Bandage: a dressing used to cover an afflicted area.

Centrally-mediated analgesia: analgesia produced through activation of opioid receptors in the central nervous system (brain, spinal cored, epidural space, etc.).

Central opioid receptor: opioid receptor that is found in the central nervous system.

Central nervous system: the brain and spinal cord.

Dermal: relating to the dermis.

Dermis: living part of skin.

Dressing combine: designed to provide warmth and protection and to absorb large quantities of fluid that may drain from an incision or wound; consists of a nonwoven fabric cover enclosing fiber with or without absorbent tissue.

Inflammation: an immune system-mediated process characterized by redness, heat, swelling, and pain at the local site.

Mixed agonist-antagonist: referring to opioids, a compound which displays both agonist and antagonist activities at opioid receptors subtypes. Examples of opioids which are mixed agonist-antagonists include but are not limited to buprenorphine and butorphanol.

Opioid analgesic: opioids which produce an analgesic effect, generally through their interaction with opioid receptors; opioid analgesics may be opioid receptor agonists, opioid receptor partial agonists, or opioid receptor mixed agonist-antagonists.

Opioid receptor: a receptor at which an opioid binds. There are at least three separate subtyes of opioid receptors: mu ($\mu$), delta ($\delta$), and kappa ($\kappa$).

Partial agonist: a compound which produces some effects, but not others, at receptor subtypes which are known to be responsible for multiple effects. Ethylketocyclazocine is a partial opioid receptor agonist.

Perineurium: the sheath of dense connective tissue that envelops a bundle of nerve fibers composing a peripheral nerve.

Peripheral nervous system: cranial, spinal, and peripheral nerves which serve to provide a nervous connection between tissues and organs of the body and the brain.

Peripheral opioid receptor: opioid receptor located outside the central nervous system.

Sprouting: a phenomenon which occurs in inflammation which is characterized by an increase in the number of peripheral sensory nerve terminals as well as the number of peripheral opioid receptors.

Skin: the outer covering of an animal body; the outermost layer of skin is called the epidermis (non-living part) the layer beneath the epidermis is called the dermis (living part).

Therapeutically-effective amount: the amount necessary to bring about a therapeutic effect.

Transdermal: passing through the dermia.

Other terms employed herein not specifically defined immediately above are well known to those of ordinary skill in the art and/or are also further defined in the specification either expressly or indirectly.

The entire disclosures of all patents and publications, cited above and below, are hereby incorporated by reference as though set forth in full herein.

B. Illustrative Preferred Embodiments

The present invention is directed to methods of treating acne using topical opioids. In accordance with the present invention, opioids are preferably applied topically to an area which is affected by acne. Preferably, the application of opioids in accordance with the present invention results in a reduction in the number and severity of the acne lesions.

In accordance with the present invention, the opioid of choice may be an agonist, an opioid antagonist, a mixed agonist/antagonist, or a partial agonist. Preferably, the opioid used in accordance with the present invention comprises an opioid agonist. Opioid agonists include, but are not limited to, morphine, depomorphine, etorphine, heroin, hydromorphone, oxymorphone, levorphanol, methadone, levomethadyl, meperidine, fentanyl, sufentanyl, alfentanil, codeine, hydrocodone, oxycodone, and mixtures of the foregoing.

In other preferred embodiments, the opioid selected comprises a compound with mixed opioid agonist/antagonist activities, or one that exhibits only partial agonist activity. Compounds which exhibit mixed agonist/antagonist activity include, but are not limited to, buprenorphine, nalbuphine, botorphanol, pentezocine, and mixtures of such compounds. Compounds which exhibit partial agonist activity include, but are not limited to ethylketocyclazocine.

In other preferred embodiments, the opioid selected may comprise an opioid antagonist. Opioid antagonists include, but are not limited to, naloxone and naltrexone.

Other preferred opioids envisioned include, but are not limited to, natural and synthetic peptides which interact with opioid receptors. The present invention is not limited to the delivery of a single opioid; preferred embodiments include mixtures of opioid agents. The present invention is also not limited to the specific drugs mentioned herein, and derivatives that are pharmaceutically-acceptable salts, prodrugs, and other derivatives are envisioned as well. It is expected that, as medical science advances, more compounds which can be classified as opioids will be discovered. Such compounds are also envisioned to be within the scope of the present invention. The present invention is not limited solely to the delivery of opioids: other agents may be incorporated as well, including but not limited to antibiotics and/or steroids.

As noted above, the doses of opioids used in accordance with the present invention are much smaller than those doses normally used for central or systemic effects. Specifically, the present invention uses doses of opioids that are considerably lower than doses of intramuscularly (IM) administered opioids, which are given for a centrally-mediated analgesic effect. Doses used in accordance with the present invention preferably range from about $\frac{1}{1000}$ of the IM dose to about $\frac{1}{5}$ of the IM dose. More preferably, doses range from about $\frac{1}{100}$ of the IM dose to about $\frac{1}{10}$ of the IM dose. More preferably, doses range from about $\frac{1}{25}$ of the IM dose to about $\frac{1}{150}$ of the IM dose. Most preferably, doses administered in accordance with the present invention are about $\frac{1}{20}$ of the IM dose administered to achieve a centrally-mediated analgesic effect. For example, morphine is normally administered as 10 mg IM to achieve a centrally-mediated analgesic effect. In accordance with the present invention, a preferred dose of morphine would be about 0.5 mg per square inch of affected area. Butorphanol is normally administered as 2 mg IM to achieve a centrally-mediated analgesic effect. In accordance with the present invention, a preferred dose of butorphanol would be about 0.1 mg per square inch of affected area.

It should be recognized that not all opioid analgesic agents are equipotent, i.e., they do not all result in the same degree of potency for the same mass of drug. For example, the dose of butorphanol given above is about 5 times less than the dose for morphine. Therefore, when choosing the amount of opioid to be used in accordance with the present invention, the amount selected is preferably equianalgesic to the doses of opioids presented herein. Although it is not believed that the analgesic effect of the opioids used is an important part of the present invention, using equianalgesic doses has proven to be effective in choosing doses for practicing the present invention. Equianalgesic doses for opioids are well known to those of ordinary skill in the art. In addition, one of ordinary skill in the art would be readily able to determine how to use other opioids by following the present disclosure. Table 23-6, which appears on page 535 of Chapter 23, of *Goodman and Gilman's The Pharmacological Basis of Therapeutics, Ninth Edition* may be used as an aid in determining equianalgesic doses. Notation "c" of the table states:

"Except where noted, dose is the amount that produces approximately the same analgesic effect as 10 mg of morphine administered intramuscularly or subcutaneously."

Thus, the table demonstrates that, applied intramuscularly ("TM" on the Table), 10 mg of morphine provides the same analgesic effect as 130 mg of codeine, 2 mg of butorphanol, or 0.1 mg of fentanyl. In other words, to achieve the same effect, one would use thirteen times (10 mg×13=130 mg) that amount for codeine compared to the amount of morphine required, one fifth of that amount for butorphanol (10 mg×0.2=2 mg), and one one-hundredth (10 mg×0.01=0.1 mg) of that amount of fentanyl. The same types of conversions are appropriately applied in the present invention.

It is believed that the amount of opioid necessary to produce a therapeutic effect at an affected site is based on, or related to, the size of the area and the relative condition which is to be treated. For example, the amount of opioid needed to treat severe inflammatory acne is likely greater than the amount of opioid needed to treat mild to moderate acne. In addition an acute condition will likely require less medication for less time than a chronic condition. In terms of the present invention, the preferred dosage range is preferably determined by considering the amount of opioid delivered, in milligrams, and the area of the skin surface to be treated according to the present invention. In preferred embodiments, the dose is equianalgesic to up to about 5 mg morphine/6 in$^2$ of skin. More preferably, the dose is equianalgesic to about 2–3 mg morphine/6 in$^2$ of skin.

In accordance with the present invention, the foregoing doses can be readily optimized following the teachings herein, based on known pharmacological protocol, by those of ordinary skill in the art, with no more than routine optimization. Of course, the preferred lower limit for drug delivery is that necessary to bring about an anti-acne effect. The preferred upper limit is less than that amount which produces systemic effects.

For those opioids which do not produce an analgesic effect, such as opioid antagonists which include but are not limited to naloxone and naltrexone, the opioid should be mixed in the carrier vehicle in the range of about 0.01% by weight to about 5% by weight. Preparations containing naloxone and naltrexone are preferably applied in the same manner and in the same amounts as the other opioids set forth herein.

Regardless of which opioid is used in accordance with the present invention, a preferably dose is that which produces a therapeutic effect. Different opioids will likely be used in different amounts, and even according to different administration schedules. In accordance with the present invention, an opioid may be applied only once daily in a higher dose, or several times daily in a lower dose. Alternatively, it may be determined that a therapeutic effect can be achieved by the administration of a lower dose only once daily. For other patients, a higher dose administered several times daily may be necessary. Many combinations of dose and administration schedule are acceptable within the scope of the present invention. The only requirement is that the dose be delivered in a schedule which produces a therapeutic effect. Of course, the lower limit for administration is that which will produce a therapeutic effect.

Certain embodiments of the present invention comprise any topically acceptable non-transdermally effective carrier vehicle. Preferred topically acceptable vehicles include but are not limited to gels, lotions, creams, ointments, and liquids. Administration of the preferred embodiment is performed in accordance with that mode which is most amenable to the topically acceptable form chosen. For example, gels, lotions, creams, and ointments are preferably administered by spreading. Liquids are preferably administered by spraying.

Although it is not crucial, the dilution of the opioid in the carrier vehicle can be an important concentration in the vehicle should be high enough that the patient does not need to wait an excessively long time for the vehicle to dry. On the other hand, the opioid concentration should be dilute enough that a patient can achieve effective coverage of the affected area. Suitable vehicles include aqueous creams and alcoholic sprays (e.g., sprays comprising acholic solutions) or gels. Additionally, the vehicle could include a component which polymerizes in response to exposure to air or ultraviolet radiation.

The amount of vehicle to be applied will vary depending on the choice of vehicle as well. For example, when the opioid is administered by spraying an alcoholic liquid solution of the drug, the total volume in a single dose may be as low as 0.1 ml. Conversely, when the opioid is administered in an aqueous cream, the total volume may be as high as 1 ml. It has been found that a total volume for application of K-Y Jelly™ is preferably about 0.5 ml/in$^2$ of skin. Of course, if a large contiguous area is affected, a larger application volume may be necessary. Conversely, if the acne lesions are scattered, the volume applied may be smaller. The carrier selected and its manner of application are preferably chosen in consideration of the needs of the patient and the preferences of the administering physician.

In accordance with the present invention, an opioid preparation is applied to the affected area regularly until relief is obtained. Preferably, such regular application comprises application from one to five times per day. However, other application schedules may be utilized in accordance with the present invention.

Other embodiments of the present invention include dressings that may be placed on the affected area and remain there to release opioid onto the affected area. Preferably, such embodiments include but are not limited to, bandages, surgical dressings, gauzes, patches, and sterile adhesive strips. Preferred dressings are treated with opioids prior to application to the affected area. The dressing preferably acts as a protective barrier to the area, preventing the opioid from being wiped away. Such embodiments are especially useful for overnight application to an affected area. However, these preferred embodiments might also find application in daily use. Preferred dressings may be pretreated with opioids by a manufacturer and packaged as ready to use. Alternatively, a subject may apply a gel, cream, lotion, or ointment prepared in accordance with the present invention to a dressing which is then applied to the affected area.

When administered in accordance with the present invention, treatment will result in therapeutic effects which include an anti-acne effect. Therapeutic effects in the affected area include, but are not limited to, decrease in redness, decrease in swelling, and decrease in inflammation. When an opioid analgesic preparation is used, therapeutic effects in the affected area include decrease in pain. These therapeutic effects are observed when treatment in accordance with the present invention is made to any of the suitable conditions.

The present invention is not limited to the treatment of acne vulgaris and is also directed to the treatment of neonatal and infantile acne, perioral dermatitis, acne conglobata, hidrandenitis suppurativa, acne fulminens, pyoderma faciale, acne excorieé des jeunes filles, acne mechanica, acne tropicalis, acne aestivalis, favré-racouchot syndrome, drug-induced acne, acne cosmetica, pomade acne, occupational acne, chloracne, steroid acne, rosacea, acne keloidalis nuchae and gram-negative folliculitis. The procedures followed for treatment of these diseases are the same as those set forth for the treatment of acne vulgaris set forth herein. The present invention is also useful in the treatment of other conditions in which local inflammation or local infection are present. Such other conditions include Staphylococous infections, various herpes and other viral infections, and burns. Local inflammation which is the result of noxious stimuli can also be treated in accordance with the present invention. Such noxious stimuli include irritation and inflammation resulting from contact with chemicals or other irritants. Inflammation resulting from contact with poison ivy, or other plants, is also treatable in accordance with the present invention. Other sources of inflammation treatable in accordance with the present invention include stings from insects.

The foregoing specific embodiments are illustrative of applications in which methods of treating acne using opioids in accordance with the present invention can be employed. Those of ordinary skill in the art will readily understand that other manners of administration of opioids to treat acne are suitable and are in accordance with the present invention as well.

Without further elaboration, it is believed that one skilled in the art can, using the preceding description, utilize the present invention to its fullest extent.

The following preferred working examples are, therefore, to be construed as merely illustrative, and not limitative of the remainder of the disclosure in any way whatsoever.

Various attempts were made to test the invention. Representative examples of the results are set forth in the Examples and in Table I. In particular, patients with various types of acne who had tried several different treatments including benzoyl peroxide, tretinoin, and antibiotics, were quite distraught with their appearance. These patients were treated with various treatment regimens, all with unexpected, surprisingly quite good results. Table I shows the results from a representative sample of patients treated in accordance with the present invention.

EXAMPLES

Example 1

Morphine Sulfate for the Treatment of Acne Vulgaris of the Face

The first study of a patient using the topical application of an opioid for acne involved a 13 year old girl with mild-to-moderate acne vulgaris of the face. The patient had tried benzoyl peroxide with little or no success immediately prior to treatment according to the present invention. This agent was producing unpleasant side effects which included dryness of the skin as well as itching and peeling.

Treatment was initiated using a mixture of 10 ml of K-Y Jelly and 10 mg morphine sulfate, which is readily soluble in the K-Y Jelly at that concentration. Treatment included application of approximately 0.5 ml of the mixture twice daily. Lesions on the face dried significantly within a day, and completely disappeared within 3 days. Side effects were nonexistant and additional treatment was unnecessary.

Example 2

Butorphanol for the Treatment of Acne Vulgaris of the Face

In order to determine if other opioids were equally effective, a patient (femal, 27 years old), was treated using a different opioid preparation. The patient exhibited mild-to-moderate acne vulgaris of the face. The patient had tried topical tretinoin and benzoyl peroxide with little or no success prior to treatment according to the present invention. These agents were producing unpleasant side effects which included dryness, itching, and peeling of the skin.

Treatment was initiated using a mixture of 30 ml of K-Y Jelly and 6 mg butorphanol, which is readily soluble in the K-Y Jelly at that concentration. Treatment included application of approximately 0.5 ml of the mixture twice daily. Lesions on the face dried significantly with a day, and completely disappeared within 3 days. Side effects were nonexistent and additional treatment was unnecessary.

Example 3

Morphine for the Treatment of Acne Vulgaris of the Chest

In order to determine if treatment of other parts of the body would be equally successful, a patient (female, 25 years old), was treated using a different opioid preparation. The patient exhibited mild-to-moderate acne vulgaris of the chest. The patient had tried benzoyl peroxide with little or no success and was using benzoyl peroxide immediately prior to treatment according to the present invention. Use of benzoyl peroxide was producing unpleasant side effects which included dryness, itching, and peeling of the skin.

Treatment was initiated using a mixture of 10 ml of K-Y Jelly and 10 mg morphine, which is readily soluble in the K-Y Jelly at that concentration. Treatment included application of approximately 0.5 ml of the mixture twice daily. Lesions on the chest dried significantly with a day, and completely disappeared within 3 days. Side effects were nonexistent and additional treatment was unnecessary.

Example 4

Butorphanol for the Treatment of Cystic Acne of the Face

In order to determine if cystic acne would be responsive to treatment with opioids, a fourth 17-year old male patient was treated using a butorphanol preparation. The patient exhibited moderate-to-severe cystic acne of the face. The patient had tried benzoyl peroxide with little or no success prior to treatment according to the present invention. This agent was producing unpleasant side effects which included itching and peeling of the skin, as well as dryness of the skin.

Treatment was initiated using a mixture of 30 ml of K-Y Jelly and 6 mg butorphanol, which is readily soluble in the K-Y Jelly at that concentration. Treatment included application of approximately 0.5 ml of the mixture 2–3 times daily. Lesions on the face decreased in redness and swelling by approximately 50% after 2 days treatment. Side effects were nonexistent and additional treatment was unnecessary.

All of the foregoing acne patients treated according to the present invention (including those in the Examples above and those represented in Table I) stated the following: 1) The medication was only applied two or three times daily. The amount used was enough to cover the affected area and not more. 2) Starting at the point the treatment was initiated, growth of the lesion ceased. 3) In cases of mild-to-moderate acne, the lesions dried quickly, and disappeared within two to three days. 4) In cases of moderate-to-severe acne, the lesions reduced in redness and swelling by about 50% within two to three days. 5) No side effects were observed from the treatment, including no itching and no peeling. Patients unanimously stated that the treatment according to the present invention was a significant improvement over their previous treatment because relief of the condition was observed without the side effects of other treatments. In addition, relief of the symptoms was more rapid when treated in accordance with the present invention. Representative data from the foregoing examples are summarized below in Table I.

Example 5

Butorphanol for the Treatment of Herpes Zoster of the Face, Neck, and Arm

In order to determine if herpes zoster would be responsive to treatment with opioids, a patient (female, 78 years old), was treated using a butorphanol preparation. The patient exhibited herpes zoster characterized by puffy lesions, with pussy, crusty lesions, and severe pain. The patient had tried oral anti-viral medication and pain medication with little or no success prior to treatment according to the present invention.

Treatment was initiated using a mixture of 30 ml of K-Y Jelly and 6 mg butorphanol, which is readily soluble in the K-Y Jelly at that concentration. Treatment included application of the mixture 2–3 times daily. A week after treatment was initiated, all of the pussiness and crustiness had gone and the lesions had cleared with no oozing.

Example 6

Butorphanol for the Treatment of Herpes Zoster of the Back and Abdomen

A 73-year old female patient was presented with a severe (level T10, T11, and T12) attack of herpes zoster. The patient had tried oral anti-viral medication with little or no relief.

Treatment was initiated with a mixture of 30 ml of K-Y Jelly with 6 mg butorphanol, applied in small doses three times daily. Within a week the patient reported that the lesions had disappeared without pus or oozing, and that normal clothing could again be worn.

Example 7

Morphine for the Treatment of Genital Herpes

In order to determine if genital herpes would be responsive to treatment with opioids, a 27-year old female patient was treated using a morphine preparation. The patient stated that attacks generally lasted 8–10 days, and include symptoms of severe pain upon urination. The patient had tried oral anti-viral medication without any success.

The patient was given 30 ml of K-Y Jelly with 30 mg morphine to apply. The patient applied the preparation in the morning and at night before sleep. In a follow-up visit the following week, the patient stated that pain had been relieved within the first day and that lesions had cleared in three days.

Example 8

Morphine for the Treatment of Genital Herpes and Herpes Zoster

A 32-year old male patient was presented with symptoms of both genital herpes and herpes zoster. The patient reported that normally the lesions had taken 8–11 days to disappear and that the lesions were quite painful. Oral anti-viral medications were of no avail.

Treatment was initiated using a mixture of 30 ml K-Y Jelly and 30 mg morphine. The patient was given the mixture to apply three times daily. At a follow-up visit the following week the patient reported that the lesions had disappeared within three days, and that the pain had disappeared after only a few applications.

From the foregoing Examples directed at the use of opioids for the treatment of herpetic lesions, it is clear that opioids can expedite the remission of such lesions. Herpetic lesions treated in accordance with the present invention will generally disappear twice as quickly as those treated by conventional methods.

Example 9

Morphine for the Treatment of Burns

In order to determine if burns could be effectively treated according to the present invention, a three-year old baby was treated for severe burns to the back from spillage of hot coffee. Upon arrival at the clinic, the patient had been treated with ice, xylocaine gel, and other medications by paramedics, with no relief.

Treatment was initiated with 4 ml K-Y Jelly containing 4 mg morphine to the affected area. Within 20 minutes the child had fallen asleep.

Upon examination the following day, the patient had no apparent lesions of the back, and there were no marks of the burn. Topical application the preparation was maintained for approximately two days. After approximately three days of periodic application, there were no visible signs of the burn despite the fact that it appeared to have been between second- and third-degree.

Example 10

Morphine for the Treatment of Burns

A 42-year old male patient was treated for a second-degree burn of the arm caused by an autoclave. The patient complained of severe pain. Second-burns normally take more than a week to heal and can cause significant scarring.

Treatment was initiated using a mixture of 1 ml of K-Y Jelly with 1 mg morphine. As early as the following day, the lesion had disappeared. No long-term visual effects were observed.

Example 11

Morphine for the Treatment of Burns

A 41-year old male patient was presented with a burn from an autoclave. The burn was ½ inch in width and 2 inches in length.

Within 20 minutes of the application of 1 mg morphine in 1 ml K-Y Jelly the pain had disappeared. There was no need for further application and the lesion was not apparent the following day.

From the foregoing Examples directed at the use of opioids for the treatment of burns, it is clear that opioids can expedite the healing of such burns. Burns treated in accordance with the present invention will generally disappear at least twice as quickly as those treated by conventional methods. In addition, whereas normally burns can leave significant scars in the burned area, burns treated in accordance with the present invention will scar significantly less than those burns left untreated.

From the foregoing Examples, it is clear that the use of opioids in accordance with the present invention can improve the healing of inflammatory conditions of the skin. Depending on the condition, the improved healing is manifest in different manners. For acne, a decrease in the number of lesions, redness, and swelling, is apparent more rapidly than when the lesions are left untreated or when the lesions are treated with over-the-counter preparations. For herpetic lesions, the lesions decrease in number, size, redness, swelling, crustiness and pusiness, and generally go into remission faster than when left untreated. Burn tissue heals more quickly than when treated in other manners, and scarring is significantly decreased. Generally, treatment in accordance with the present invention will result in a shortened healing time.

From the foregoing descriptions, one skilled in the art can easily ascertain the essential characteristics of this invention, and without departing from the spirit and scope thereof, can make various changes and modifications to the invention to adapt it to various usages and conditions. Specifically, the foregoing can be applied to similar diseases (such as Staphylococcus infections and other skin inflammation) by following the foregoing procedures and applying routine standard pharmacological protocol.

Although the invention has been described with reference to particular embodiments, it is to be appreciated that various adaptations and modifications may be made and the invention is only to be limited by the appended claims.

TABLE I

| | Age | Sex | Condition | Preparation | Result | Additional Treatment | Side Effects | Compared to Other Topical Preparations | Amount Used |
|---|---|---|---|---|---|---|---|---|---|
| 1 | 13 | F | acne vulgaris (face) | 10 ml KY-Jelly/ 10 mg morphine sulfate | lesions dried next day and disappeared in 3 days | none | none | no itching no peeling much better results | 0.5 ml K-Y Jelly/0.5 mg morphine sulfate |

TABLE I-continued

| | Age | Sex | Condition | Preparation | Result | Additional Treatment | Side Effects | Compared to Other Topical Preparations | Amount Used |
|---|---|---|---|---|---|---|---|---|---|
| 2 | 27 | F | acne vulgaris (face) | 30 ml KY-Jelly/ 6 mg butorphanol | lesions dried next day and disappeared in 3 days | none | none | no itching no peeling much better results | 0.5 ml K-Y Jelly/0.1 mg butorphanol |
| 4 | 17 | M | acne vulgaris (face) | 10 ml KY-Jelly/ 10 mg morphine | lesions dried next day and disappeared in 3 days | none | none | no itching no peeling much better results | 0.5 ml K-Y Jelly/0.5 mg morphine |
| 5 | 28 | F | acne vulgaris (face) | 10 ml KY-Jelly/ 6 mg morphine | lesions dried next day and disappeared in 3 days | none | none | no itching no peeling much better results | 0.5 ml K-Y Jelly/0.5 mg morphine |
| 6 | 25 | F | acne vulgaris (chest) | 10 ml KY-Jelly/ 10 mg morphine | lesions dried next day and disappeared in 3 days | none | none | no itching no peeling much better results | 0.5 ml K-Y Jelly/0.5 mg morphine |
| 7 | 17 | F | acne vulgaris (chest) | 10 ml KY-Jelly/ 10 mg morphine | lesions dried next day and disappeared in 3 days | none | none | no itching no peeling much better results | 0.5 ml K-Y Jelly/0.5 mg morphine |
| 8 | 17 | F | cystic acne (face) | 30 ml KY-Jelly/ 6 mg butorphanol | 50% reduction in redness and swelling after 2 days of treatment | none | none | no itching no peeling much better results | 0.5 ml K-Y Jelly/0.1 mg butorphanol |
| 9 | 21 | F | cystic acne (face) | 30 ml KY-Jelly/ 6 mg butorphanol | 50% reduction in redness and swelling after 2 days of treatment | none | none | no itching no peeling much better results | 0.5 ml K-Y Jelly/0.1 mg butorphanol |
| 10 | 42 | F | cystic acne (face) | 30 ml KY-Jelly/ 6 mg butorphanol | 50% reduction in redness and swelling after 2 days of treatment | none | none | no itching no peeling much better results | 0.5 ml K-Y Jelly/0.1 mg butorphanol |
| 11 | 17 | M | cystic acne (face) | 30 ml KY-Jelly/ 6 mg butorphanol | 50% reduction in redness and swelling after 2 days of treatment | none | none | no itching no peeling much better results | 0.5 ml K-Y Jelly/0.1 mg butorphanol |
| 12 | 18 | F | acne vulgaris (face) | 30 ml KY-Jelly/ 6 mg butorphanol | lesions dried next day and disappeared in 3 days | none | none | no itching no peeling much better results | 0.5 ml K-Y Jelly/0.1 mg butorphanol |
| 13 | 14 | F | acne vulgaris (face) | 10 ml KY-Jelly/ 10 mg morphine | lesions dried next day and disappeared in 3 days | none | none | no itching no peeling much better results | 0.5 ml K-Y Jelly/0.5 mg morphine |
| 14 | 18 | F | cystic acne (face) | 30 ml KY-Jelly/ 6 mg butorphanol | 50% reduction in redness and swelling after 2 days of treatment | none | none | no itching no peeling much better results | 0.5 ml K-Y Jelly/0.1 mg butorphanol |
| 15 | 42 | F | cystic acne (face) | 30 ml KY-Jelly/ 8 mg morphine sulfate | lesions dried next day and disappeared in 3 days | none | none | no itching no peeling much better results | 0.5 ml K-Y Jelly/0.13 mg morphine sulfate |

What is claimed is:

1. A method of treating acne in a patient in need of such treatment comprising topically administering a therapeutically effective amount of a composition comprising an opioid.

2. The method of claim 1, wherein said composition comprises a gel or cream.

3. The method of claim 2, wherein said gel or cream is administered by spreading the gel or cream onto the affected area.

4. The method of claim 1, wherein said composition comprises a liquid.

5. The method of claim 4, wherein said liquid is administered by spraying onto the affected area.

6. The method of claim 1, wherein the opioid is administered in an amount analgesically equivalent to up to 5 mg of morphine per 6 in² of skin.

7. The method of claim 6, wherein the opioid is administered in an amount analgesically equivalent to 2–3 mg of morphine per 6 in² of skin.

8. The method of claim 1, wherein the opioid comprises morphine.

9. The method of claim 1, wherein the opioid comprises morphine sulfate.

10. The method of claim 1, wherein the opioid comprises butorphanol.

11. The method of claim 1, wherein a unit dose of said opioid is in the range of from about 1/1000 of an analgesically effective intramuscular dose of said opioid to about 1/5 of an analgesically effective intramuscular dose of said opioid.

12. The method of claim 11, wherein a unit dose of said opioid is in the range of from about 1/100 of an analgesically effective intramuscular dose of said opioid to about 1/10 of an analgesically effective intramuscular dose of said opioid.

13. The method of claim 12, wherein a unit dose of said opioid is in the range of from about 1/25 of an analgesically effective intramuscular dose of said opioid to about 1/15 of an analgesically effective intramuscular dose of said opioid.

14. The method of claim 13, wherein a unit dose of said opioid is about 1/20 of an analgesically effective intramuscular dose of said opioid.

15. The method of claim 1, wherein the acne comprises inflammatory acne.

16. The method of claim 1, wherein the acne comprises non-inflammatory acne.

17. The method of claim 1, wherein administration is via a topical dressing.

18. The method of claim 1, wherein treatment is accomplished in the substantial absence of transdermal delivery of the opioid.

19. The method of claim 18, wherein said composition comprises a gel or cream.

20. The method of claim 19, wherein said gel or cream is administered by spreading the gel or cream onto an affected area.

21. The method of claim 18, wherein said composition comprises a liquid.

22. The method of claim 21, wherein said liquid is administered by spraying onto an affected area.

23. The method of claim 18, wherein the opioid is administered in an amount analgesically equivalent to up to 5 mg of morphine per 6 in² of skin.

24. The method of claim 23, wherein the opioid is administered in an amount analgesically equivalent to 2–3 mg morphine per 6 in² of skin.

25. A method of treating skin disorders involving sebaceous glands and follicles in a patient in need of such treatment, comprising applying a therapeutically-effective amount of a composition comprising an opioid.

26. The method of claim 25, wherein treatment is accomplished in the substantial absence of transdermal delivery of the opioid.

* * * * *